United States Patent
LeHuec et al.

(10) Patent No.: US 8,070,784 B2
(45) Date of Patent: Dec. 6, 2011

(54) PLATING SYSTEM FOR STABILIZING A BONY SEGMENT

(75) Inventors: Jean-Charles LeHuec, Pessac (FR); Curtis A. Dickman, Phoenix, AZ (US); Mingyan Liu, Bourg la Reine (FR); Loic Josse, Palaja (FR); Eric C. Lange, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1506 days.

(21) Appl. No.: 11/283,350

(22) Filed: Nov. 18, 2005

(65) Prior Publication Data
US 2006/0074420 A1    Apr. 6, 2006

Related U.S. Application Data

(62) Division of application No. 10/219,516, filed on Aug. 15, 2002, now Pat. No. 6,989,012.

(60) Provisional application No. 60/396,251, filed on Jul. 16, 2002.

(51) Int. Cl.
*A61F 2/30* (2006.01)
(52) U.S. Cl. ....................................................... 606/289
(58) Field of Classification Search .................... 606/70, 606/71, 280–299
See application file for complete search history.

(56) References Cited

U.S. PATENT DOCUMENTS

| | | | |
|---|---|---|---|
| 3,659,595 A | 5/1972 | Haboush | |
| 3,695,259 A | 10/1972 | Yost | |
| 3,741,205 A | 6/1973 | Markolf et al. | |
| 4,488,543 A | 12/1984 | Tornier | |
| 4,794,918 A * | 1/1989 | Wolter | 606/295 |
| 4,938,769 A | 7/1990 | Shaw | |
| 4,944,757 A | 7/1990 | Martinez et al. | |
| 4,957,497 A | 9/1990 | Hoogland et al. | |
| 4,963,152 A | 10/1990 | Hofmann et al. | |
| 5,061,271 A | 10/1991 | Van Zile | |
| 5,127,914 A | 7/1992 | Calderale et al. | |
| 5,147,361 A | 9/1992 | Ojima et al. | |
| 5,324,290 A | 6/1994 | Zdeblick et al. | |
| 5,397,363 A | 3/1995 | Gelbard | |
| 5,423,826 A | 6/1995 | Coates et al. | |
| 5,534,027 A | 7/1996 | Hodorek | |
| 5,549,612 A | 8/1996 | Yapp et al. | |
| 5,569,250 A | 10/1996 | Sarver et al. | |
| 5,601,553 A | 2/1997 | Trebing et al. | |
| 5,766,254 A * | 6/1998 | Gelbard | 623/17.16 |
| 5,785,713 A | 7/1998 | Jobe | |
| 5,800,433 A | 9/1998 | Benzel et al. | |
| 5,879,389 A | 3/1999 | Koshino | |

(Continued)

FOREIGN PATENT DOCUMENTS

DE    195 42 116 A1    5/1997

(Continued)

*Primary Examiner* — Thomas C. Barrett
*Assistant Examiner* — Christopher Beccia

(57) ABSTRACT

A plating system for stabilization of a bony segment includes a plate engageable to at least first and second bony elements. For spinal stabilization, the plate is attached at least to first and second vertebrae with at least one bone fastener in each vertebra. Retaining members are attachable to the plate to prevent the bone fasteners from backing out of the plate. One retaining member is a variable retaining member that allows the bone fasteners to toggle in the plate without interference. A second retaining member is a fixed retaining member that fixes the bone fasteners relative to the plate.

20 Claims, 10 Drawing Sheets

U.S. PATENT DOCUMENTS

| | | | |
|---|---|---|---|
| 5,904,683 A | | 5/1999 | Pohndorf et al. |
| 6,017,345 A | | 1/2000 | Richelsoph |
| 6,022,350 A | | 2/2000 | Ganem |
| 6,139,550 A | * | 10/2000 | Michelson .................. 606/70 |
| 6,152,927 A | * | 11/2000 | Farris et al. ................ 606/287 |
| 6,156,037 A | | 12/2000 | LeHuec et al. |
| 6,193,720 B1 | * | 2/2001 | Yuan et al. .................. 606/279 |
| 6,193,721 B1 | * | 2/2001 | Michelson .................. 606/70 |
| 6,206,882 B1 | * | 3/2001 | Cohen ........................ 606/283 |
| 6,224,602 B1 | * | 5/2001 | Hayes ........................ 606/296 |
| 6,228,085 B1 | * | 5/2001 | Theken et al. .............. 606/289 |
| 6,235,034 B1 | * | 5/2001 | Bray ........................... 606/71 |
| 6,258,089 B1 | | 7/2001 | Campbell et al. |
| 6,261,291 B1 | | 7/2001 | Talaber et al. |
| 6,290,703 B1 | | 9/2001 | Ganem |
| 6,306,139 B1 | * | 10/2001 | Fuentes ...................... 606/70 |
| 6,331,179 B1 | | 12/2001 | Freid et al. |
| 6,406,478 B1 | * | 6/2002 | Kuo ............................ 606/71 |
| 6,413,259 B1 | * | 7/2002 | Lyons et al. ................. 606/295 |
| 6,454,767 B2 | * | 9/2002 | Alleyne ...................... 606/279 |
| 6,602,255 B1 | * | 8/2003 | Campbell et al. ........... 606/290 |
| 6,695,846 B2 | * | 2/2004 | Richelsoph et al. ......... 606/71 |
| 2002/0022843 A1 | * | 2/2002 | Michelson .................. 606/70 |
| 2002/0147450 A1 | | 10/2002 | LeHuec et al. |

FOREIGN PATENT DOCUMENTS

| | | |
|---|---|---|
| EP | 0 455 255 A1 | 11/1991 |
| EP | 0 599 766 A1 | 6/1994 |
| EP | 0 820 730 A1 | 1/1998 |
| EP | 0 867 149 A1 | 9/1998 |
| EP | 0 988 833 A2 | 3/2000 |
| EP | 1 169 971 A2 | 1/2002 |
| FR | 2 726 755 A1 | 5/1996 |
| FR | 2 740 321 A1 | 4/1997 |
| FR | 2 778 088 A1 | 11/1999 |
| FR | 2 784 571 A1 | 4/2000 |
| FR | 2 792 185 A1 | 10/2000 |
| WO | WO 95/25474 | 9/1995 |
| WO | WO 97/37620 | 10/1997 |
| WO | WO 99/21502 | 5/1999 |
| WO | WO 00/24325 | 5/2000 |
| WO | WO 00/56653 | 9/2000 |
| WO | WO 00/78238 A1 | 12/2000 |
| WO | WO 02/080791 A1 | 10/2002 |

* cited by examiner

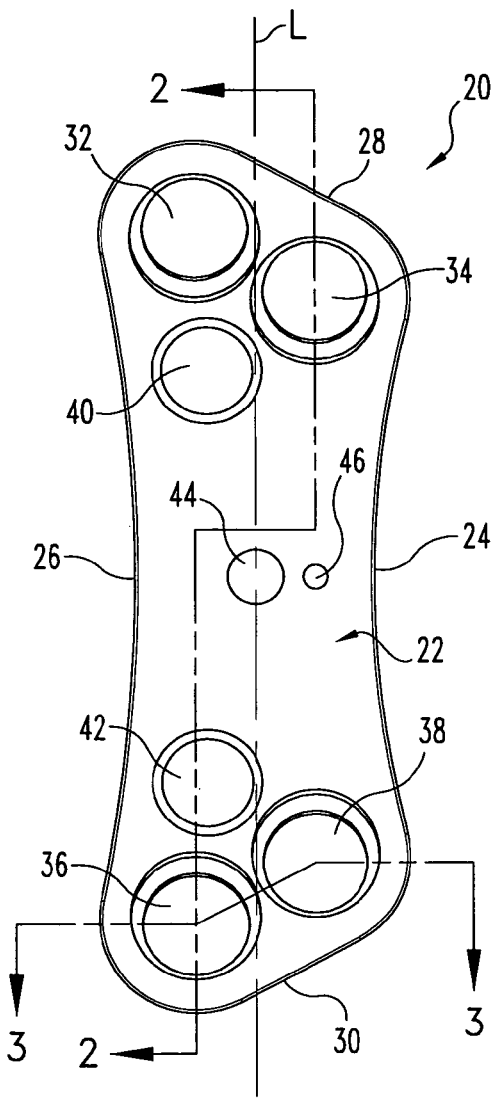
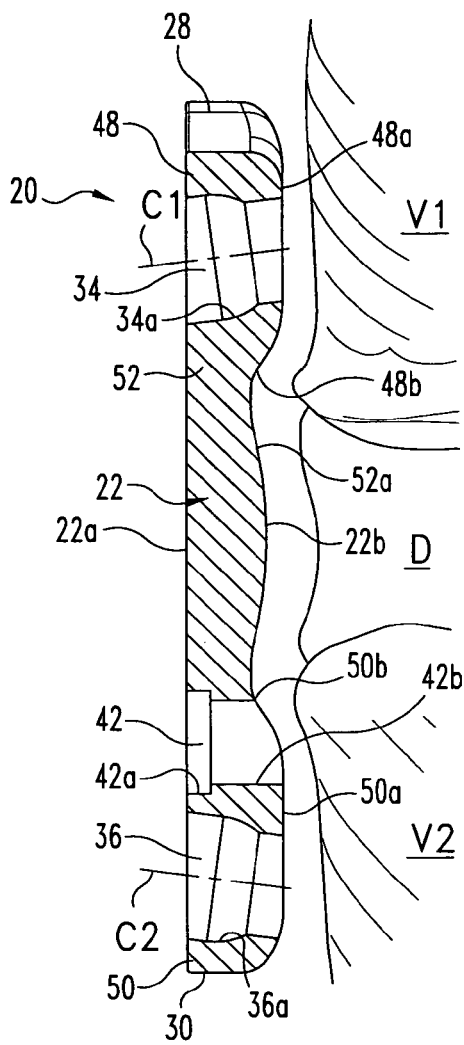
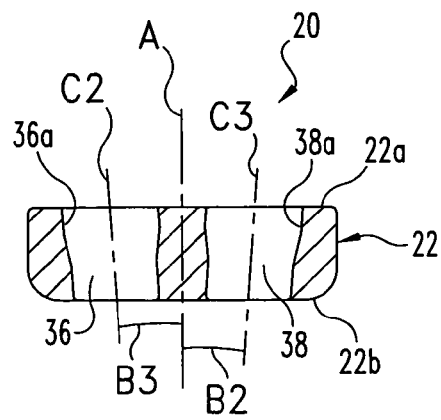
*Fig. 1*  *Fig. 2*
*Fig. 3*

PLATING SYSTEM FOR STABILIZING A BONY SEGMENT

CROSS-REFERENCE TO RELATED APPLICATIONS

This application is a divisional of U.S. patent application Ser. No. 10/219,516 filed on Aug. 15, 2002, and now issued as U.S. Pat. No. 6,989,012, which claims the benefit of the filing date of U.S. Provisional Application No. 60/396,251 filed on Jul. 16, 2002. Each of the referenced applications is hereby incorporated by reference in its entirety.

BACKGROUND

Various types of plating devices and systems have been used to stabilize portions of bones including the spine. Spinal stabilization techniques have employed plating on the posterior, anterior, lateral, postero-lateral and antero-lateral portions of a spinal column segment. Such plating systems can provide fixation of a spinal column segment for the repair of injured or diseased vertebrae, intervertebral discs, and other elements of the spinal column. Such plating systems can also be employed alone or in combination with other implants, such as other plating or fixation systems, or interbody fusion devices.

While spinal plating systems and other bone fixation systems are known, the need remains for additional improvements. The present invention is directed to satisfying this need, among others.

SUMMARY

The present invention relates generally to plating systems for stabilization of a bony segment, such as a spinal column segment.

Bone screws that secure a plate to a bony segment can back-out from the plate. One embodiment of a retaining member of the invention prevents the screws from backing out of the plate while providing clearance between the retaining plate and the screws so that the screws can pivot in the bone screw holes of the plate without interference from the retaining member. Another embodiment retaining member of the invention fixes the bone screws relative to the plate by engaging the heads of the bone screws below the upper surface of the plate, reducing the profile of the plating system above the bony segment.

According to further aspects, a plating system for stabilization of a bony segment includes a plate engageable to at least first and second bony elements. For spinal stabilization, a plate is attached at least to first and second vertebrae with at least one bone screw in each vertebra. A selected retaining member is attachable to the plate to prevent the at least one bone screw from backing out of the plate. One retaining member is a variable retaining member that allows the at least one bone screw to toggle in the plate without interference from the variable retaining member attached to the plate. A second retaining member is a fixed retaining member that fixes the at least one bone screws relative to the plate when the fixed retaining member is attached to the plate.

Instruments for inserting and attaching the plate to the bony segment, and for inserting and attaching the retaining members to the plate, are also contemplated.

Methods for inserting the plate and retaining members, and surgical methods for spinal stabilization, are further contemplated.

Further embodiments, aspects, forms, features, advantages, objects and principles of the invention will also be described below.

BRIEF DESCRIPTION OF THE DRAWINGS

FIG. 1 is a top plan view of a plate comprising a portion of the plating system of the present invention.

FIG. 2 is a sectional view of the plate through line 2-2 of FIG. 1 and positioned adjacent a bony segment.

FIG. 3 is a sectional view of the plate through line 3-3 of FIG. 1.

DESCRIPTION OF THE ILLUSTRATED EMBODIMENTS

Figure 6:
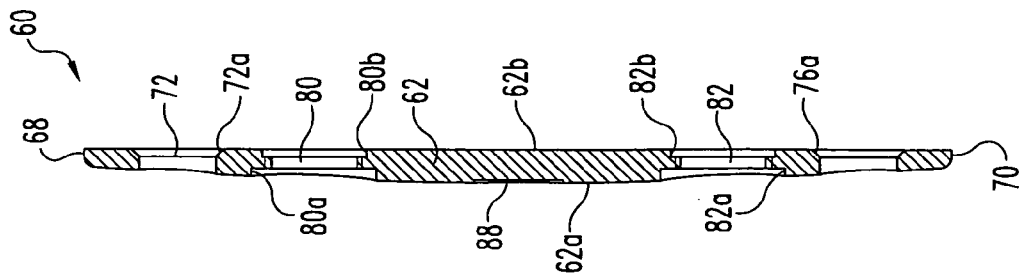
FIG. 6 is a sectional view of the retaining member through line 6-6 of FIG. 5.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices, and any such further applications of the principles of the invention as illustrated therein are contemplated as would normally occur to one skilled in the art to which the invention relates.

The invention includes a plate for attachment to a bony segment of the human body. Retaining members are provided to prevent the plate fasteners from backing out relative to the plate. The fasteners attach the plate to first and second bony segments to stabilize the bony segments relative to one another. In one application, the plate is attached to first and second vertebrae of a spinal column. In another application, the plate is attachable to the lateral or oblique aspect of the thoracic and lumbar vertebrae of the spine. Attachment to other vertebrae of the spine, and also to other aspects of the vertebrae of the spine, are also contemplated.

The plate is fixed to each bony segment by at least one fixation screw adjacent each end of the plate. In one specific embodiment, the plate includes a first portion positionable along an upper vertebra, a second portion positionable along a lower vertebra, and a middle portion therebetween extending along the spinal disc space between the adjacent vertebrae. The first portion includes a pair of holes for receiving bone fasteners to engage the plate to the upper vertebra, and the second portion includes a pair of holes for receiving bone fasteners to engage the plate to the lower vertebra.

Retaining members are provided to prevent the bone fasteners from backing out of the plate once seated thereon to engage the plate the bony segment. In one embodiment, the retaining member is a variable retaining member. The variable retaining member extends at least partially over the screw holes and prevents the screws from backing out of the plate. It is contemplated that the variable retaining member includes apertures or holes therethrough corresponding to the location of the bone fasteners that secure the plate to the bony segment. The apertures are smaller than the upper portion of the bone fasteners, yet allow the bone fasteners to pivot in the plate holes without interference from the variable retaining member. In another embodiment, a fixed retaining member is provided that includes projections extending therefrom corresponding to the locations of the bone fasteners in the plate. The projections engage an upper portion of the bone fasteners and prevent the bone fasteners from backing out of the plate and also from pivoting relative to the plate.

Referring to FIGS. 1-3, there is shown a plate 20 attachable to a bony segment. Plate 20 includes a body 22 having an upper surface 22a and an opposite lower surface 22b. Body 22 includes a first side 24 and a second side 26. First side 24 and second side 26 extend between a first end 28 and an opposite second end 30. First and second sides 24, 26 can have a concave profile to minimize the lateral extent of body 22 along the bony segment. First end 28 and second end 30 can be obliquely oriented with respect to longitudinal axis L of plate 20 such that second side 26 has a length greater than first side 24. The corners of body 22 transitioning between sides 24, 26 and ends 28, 30 can be rounded to eliminate sharp or abrupt edges which could pinch, cut or wear against tissue. The surfaces of body 22 transitioning between upper surface 22a and lower surface 22b can also be smooth and rounded to eliminate sharp or abrupt edges that could pinch, cut or wear against tissue.

Body 22 of plate 20 further includes a first portion 48, a second portion 50 and a middle portion 52 extending therebetween. Plate 20 includes a first hole 32 and a second hole 34 extending through body 22 at first portion 48 adjacent first end 28. Plate 20 also includes a third hole 36 and a fourth hole 38 extending through body 22 at second portion 50 adjacent second end 30. Holes 32, 34, 36 and 38 extend between and open at upper surface 22a and lower surface 22b. Other embodiments contemplate that a single hole is provided in one or both of the first and second portions 48, 50. Still other embodiments contemplate that more than two holes are provided in one or both of the first and second portions 48, 50.

In the illustrated embodiment of FIG. 2, plate 20 is positionable against and attachable to vertebrae V1 and V2 of a segment of the spinal column. It is contemplated that the overall configuration of plate 20 can be standardized and provided in a range of sizes, the external dimensions can also vary depending on the patient anatomy determined according to standardized measurements or pre-operative modeling of the region to be stabilized. Plate 20 can have a shape suited for attachment to first and second vertebrae of a spinal column segment in the thoracic or lumbar region. However, other shapes are also contemplated so long as the plate is attachable to the spine or other bony segment.

Lower surface 22b of body 22 is directed towards the bony segment. In the illustrated embodiment, lower surface 22b is adapted for positioning along vertebrae V1 and V2. Lower surface 22b comprises a first surface portion 48a along first portion 48, a second surface portion 50a along second portion 50, and a middle surface portion 52a along middle portion 52. First and second surface portions 48a, 50a can have a transition surface 48b, 50b that each include a convexly curved portion along longitudinal axis L. The convexly curved portion transitions into a concavely curved portion extending to middle surface portion 52a. These concavely-convexly curved transition surfaces allow body 22 to be nested against the lateral or oblique faces of vertebrae V1 and V2 adjacent the respective vertebral endplate.

Middle surface portion 52a, positionable along the spinal disc space between vertebrae V1 and V2, can be convexly curved along longitudinal axis L. Upper surface 22a and lower surface 22b of body 22 can have a generally non-curved configuration transverse to or about longitudinal axis L. Other embodiments contemplate other upper surface 22a and lower surface 22b configurations for plate 20 adapted to the anatomical location in which plate 20 is to be secured.

With reference to FIG. 2, the orientation of the plate holes along longitudinal axis L will be discussed. Holes 32 and 34 can each a have centerline, as indicated by centerline C1 of hole 34 in FIG. 2, oriented at an angle of about 6 degrees with respect to upper surface 22a toward first end 28. Holes 36 and 38 can each a have centerline, as indicated by centerline C2 of hole 38 in FIG. 2, oriented at an angle of about 6 degrees with respect to upper surface 22a toward second end 30. In the illustrated embodiment, where plate 20 is attached to a spinal column segment, the centerlines of holes 32, 34 are oriented cephaladly and the centerlines of holes 36, 38 are oriented caudally.

With reference to FIG. 3, the orientation of the plate holes about longitudinal axis L will be discussed. The adjacent hole pairs 32, 34 and adjacent hole pairs 36, 38 can have centerlines that converge below lower surface 22b of plate 20. For example, centerline C2 of hole 36 and centerline C3 of hole 38 are each oriented at an angle B2 and B3, respectively, with respect to an axis A. Axis A is centrally located and extends orthogonally through longitudinal axis L of plate 20 between upper surface 22a and lower surface 22b. In one embodiment, angles B2 and B3 are each about 6 degrees. Other embodiments of plate 20 contemplate orientations for the centerlines of fastener holes 32, 34, 36 and 38 relative to each other and relative to plate 20 other than those discussed above. For example, the centerlines of adjacent hole pairs can diverge below the plate. In another example, the centerlines of the holes can be orthogonal to either or both of the upper and lower surfaces of the plate.

Holes 32, 34, 36 and 38 can be provided with a spherically shaped seat in communication with the upper surface 22a of plate 20. For example, seat 34a of hole 34 and seat 36a of hole 36 have a spherically shaped portion that mates with a correspondingly shaped surface on the underside of the head of the bone fastener positioned therein. In this manner, the bone fasteners are capable of toggling in the corresponding hole to assume a plurality of angles relative to the corresponding central axis of the hole. In one embodiment, this range of angular movement is from 0 degrees to about 6 degrees in all directions about the corresponding axis. It is further contemplated that the seats in holes 32, 34, 36 and 38 can be positioned below upper surface 22a of body 22 such that the head or upper portion of the bone fastener positioned therein is recessed below upper surface 22a when the bone fastener is in contact with the seat in the fastener hole.

First hole 32 can be offset in the direction toward first end 28 from second hole 34, and third hole 36 can be offset in the direction toward second end 30 from fourth hole 38. The offset pair of screw holes allows each hole 32, 34 of the adjacent hole pair in upper portion 48, and each hole 36, 38 of the adjacent hole pair in lower portion 50, to be closely positioned to longitudinal axis L. In this manner, the lateral width of body 22 of plate 20 can be minimized while the structural integrity of body 22 between the hole pairs is maintained.

Plate 20 includes a first bore 40 extending therethrough from upper surface 22a in first portion 48 adjacent first and second holes 32, 34. Plate 20 also has a second bore 40 extending therethrough from upper surface 22a in second portion 50 adjacent third and fourth holes 36, 38. Bores 40, 42 extend through plate 20 or a sufficient distance to receive a portion of a fastener to engage a retaining member to plate 20, as discussed further below. As shown in FIG. 2 with reference to bore 42, bores 40, 42 can each be provided with an enlarged portion 42a adjacent upper surface 22a, and can have a lower portion 42b threaded or otherwise configured for engagement with the retaining member fastener 90. Enlarged portion 42a allows the fastener 90 to be centered and properly aligned in bore 42 before engagement with threaded portion 42b.

Plate 20 includes a receptacle 44 centrally located on body 22 and opening at upper surface 22a. Receptacle 44 can be threaded or otherwise configured to engage an insertion instrument for placing plate 20 adjacent the bony segment. Adjacent to and laterally offset from receptacle 44 is an adjacent alignment receptacle 46. It is contemplated receptacles 44, 46 can extend completely through plate 20 or at least far enough therein enough to accommodate insertion instruments, as discussed further below. Other embodiments of plate 20 contemplate other means for positioning plate 20 adjacent the bony segment are contemplated. For example, an insertion instrument could be provided that grasps the sides and/or the ends of plate 20, or engages one or more of the bores 40, 42 or the holes 32, 34, 36, 38.

Figure 5:
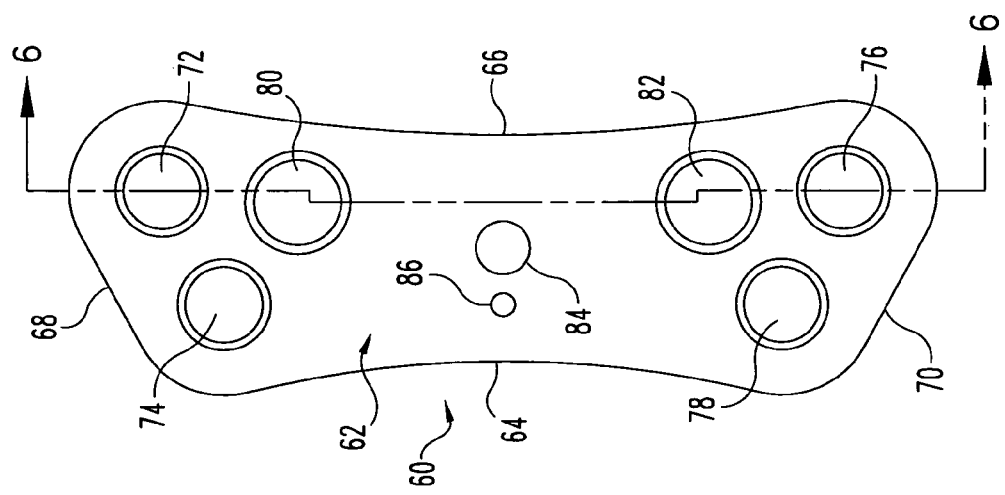
FIG. 5 is a bottom plan view of the retaining member of FIG. 4.
Figure 4:
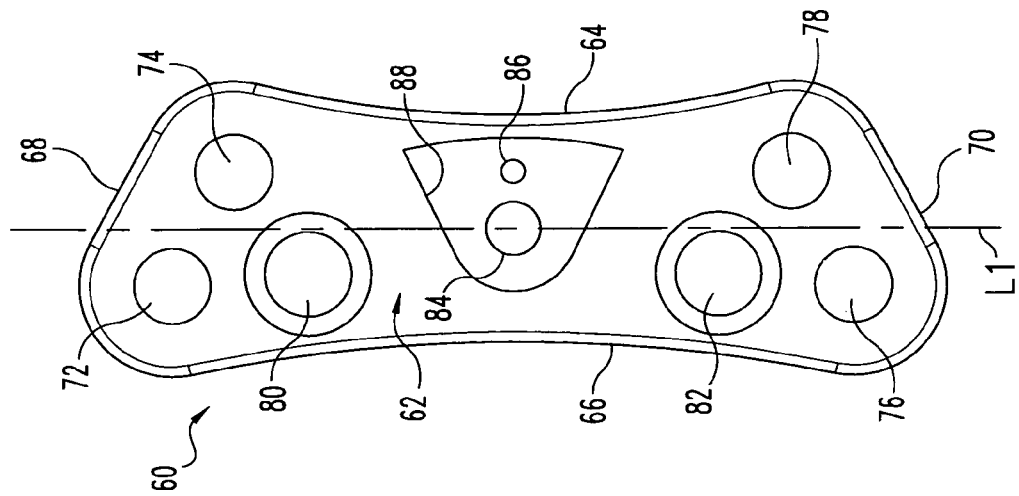
FIG. 4 is a top plan view of a first embodiment retaining member comprising a portion of the plating system of the invention.
Figure 7:
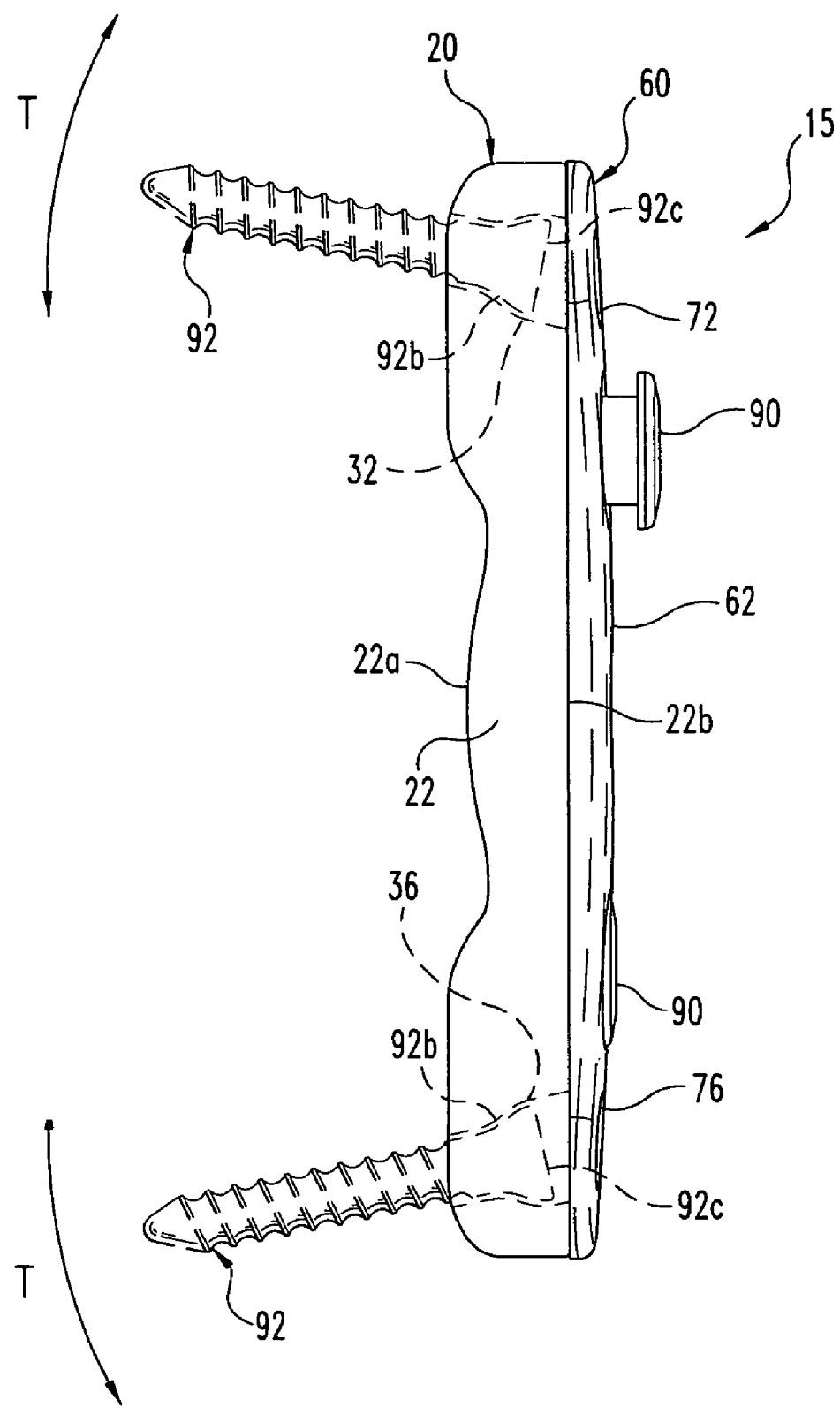
FIG. 7 is a side elevation view of the plate of FIG. 1 with bone fasteners having the first embodiment retaining member of FIG. 4 partially attached thereto along an upper surface of the plate.
Figure 8:
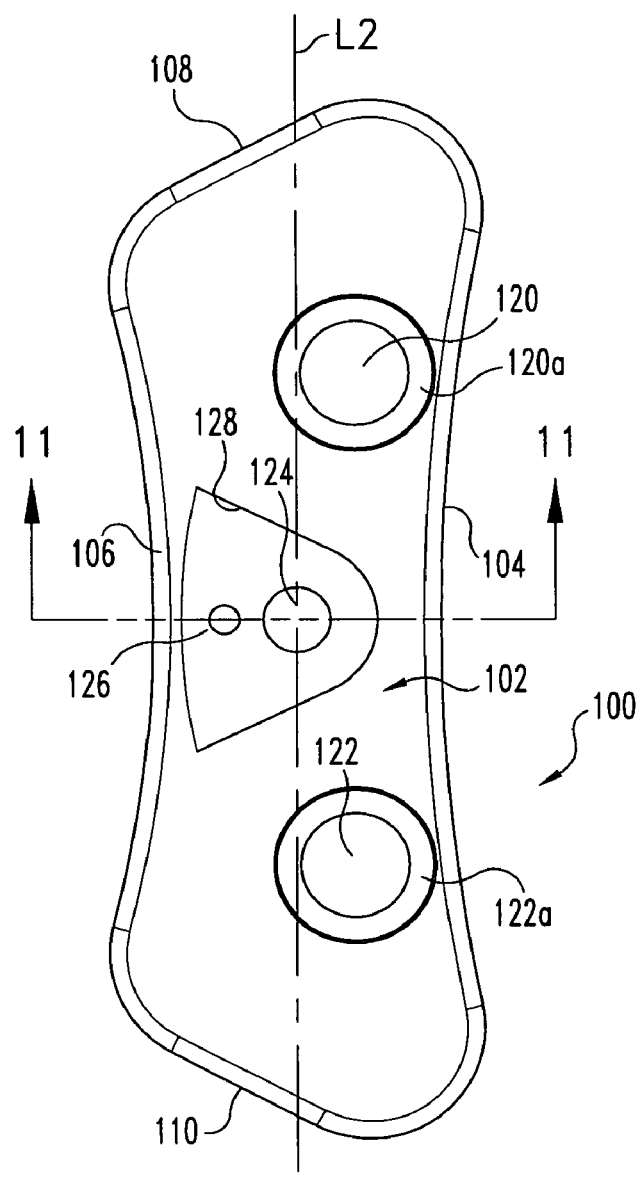
FIG. 8 is a top plan view of a second embodiment retaining member comprising a portion of the plating system of the present invention.
Figure 10:
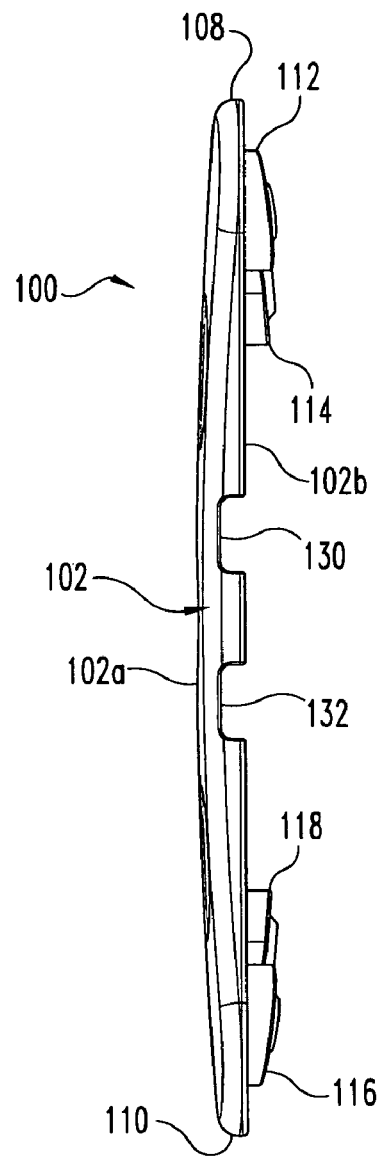
FIG. 10 is a side elevation view of the retaining member of FIG. 8.
Figure 9:
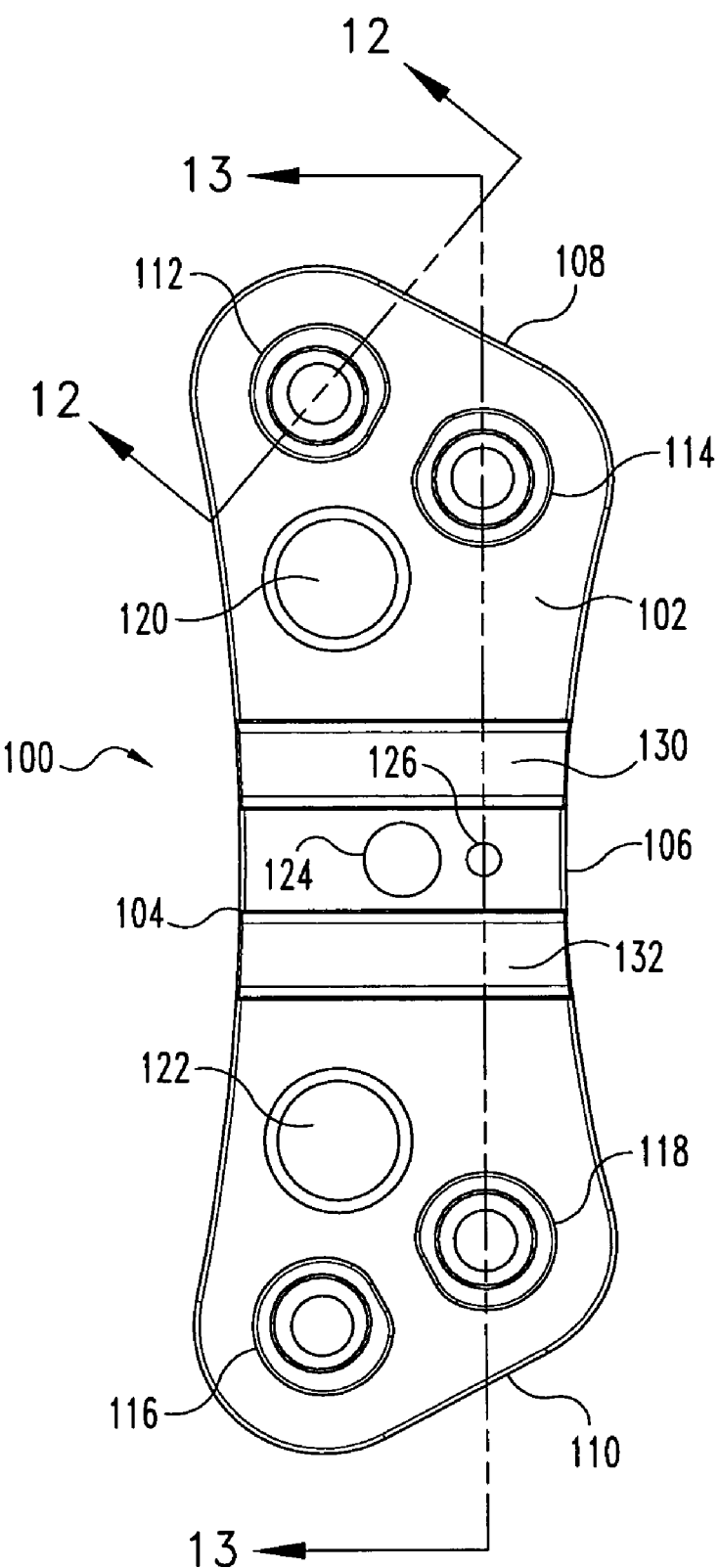
FIG. 9 is a bottom plan view of the retaining member of FIG. 8.
Figure 11:
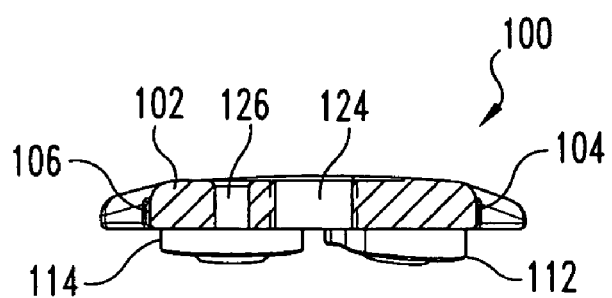
FIG. 11 is a sectional view of the retaining member through line 11-11 of FIG. 8.

Referring now to FIGS. 4-6, there is shown a first embodiment retaining member 60 attachable to plate 20, as shown in FIG. 7. Retaining member 60 includes a body 62 bounded by first and second concave sides 64 and 66 and opposite first and second ends 68 and 70, respectively. First and second ends 68, 70 can be obliquely oriented with respect to longitudinal axis L1 of retaining member 60. The size and shape of retaining member 60 can thus correspond in size and shape with plate 20. Other embodiments of retaining member 60 contemplate that its size and shape can be different than the size and shape of plate 20.

Retaining member 60 includes a pair of adjacent first and second apertures 72 and 74, and a pair of adjacent third and fourth apertures 76 and 78. Apertures 72, 74, 76, 78 are alignable with holes 32, 34, 36, 38, respectively, of plate 20 when retaining member 60 is secured thereto. More or less apertures in retaining member 60 can be provided, depending on the number of bone fastener holes of plate 20, and whether the retaining member 60 is provided with same number of apertures as bone fastener holes in plate 20. Retaining member 60 further includes a first through-hole 80 adjacent first and second apertures 72, 74, and a second through-hole 82 adjacent third and fourth apertures 76, 78. Through-holes 80 and 82 can be provided with an enlarged upper portions 80a, 82a, respectively, to recess the head of locking fasteners 90 and provide a low profile along the upper surface 62a of retaining member 60. Through-holes 80, 82 can also be provided with enlarged lower portion 80b, 82b and a thread pattern between the upper and lower portions so that the locking fastener is threadingly inserted through the respective through-holes.

Upper surface 62a of retaining member 60 can have a slight convex curvature along longitudinal axis L1. Lower surface 62b can be flat for positioning against a flat upper surface 22a that can be provided on plate 20. Retaining member 60 has a thickness between upper surface 62a and lower surface 62b sufficient to adequately resist bending and other deformations that might be created by loads on retaining member 60, yet provide as low profile as possible extending above plate 20.

Retaining member 60 further includes a recessed surface 88 in upper surface 62a. Recessed surface 88 is flat and provides an attachment location for an insertion instrument. A central receptacle 84 and an adjacent alignment receptacle 86 extend between upper surface 62a and lower surface 62b. Receptacles 84, 86 provide locations for attachment and alignment of retaining member 60 to an insertion instrument, as discussed further below. Central receptacle 84 can be threaded to facilitate attachment of retaining member 60 to the insertion instrument. Alignment receptacle 86 can be beveled adjacent upper surface 62a to facilitate insertion of an alignment member of the insertion instrument.

As shown in FIG. 7, bone fasteners 92 attach body 22 of plate 20 to the bony segment. Bone fasteners 92 can be cancellous bone screws. It is further contemplated that plate 20 can be attached with any type of bone engaging fastener, such as anchors or bolts, for example. The underside of the heads 92b of bone fasteners 92 can be rounded above the smooth shank portions of the screws received in the holes 32, 34, 36, and 38. The rounded heads 92b allow the fasteners to become well seated in seats formed in plate 20 around holes 32, 34, 36, and 38, thus permitting variable angulation or toggling of the fasteners relative to the plate 20 during and after installation of the screws. Retaining member 60 is attached to plate 20 with one or more locking fasteners 90. In the illustrated embodiment, locking fasteners 90 are set screws having a shaft threadingly engaged in a corresponding one of the bores 40, 42 of plate 20 and an enlarged head positioned in enlarged upper portions 80a, 82a of through-holes 80, 82 of retaining member 60.

Apertures 72, 74, 76 and 78 are positioned over a corresponding one of the holes 32, 34, 36 and 38 of plate 20 when retaining member 60 is attached to plate 20 with locking fasteners 90. Apertures 72, 74, 76, 78 prevent the head 92b of each bone fastener 92 in each of the holes 32, 34, 36, 38 from contacting retaining member 60 during toggling, thus allowing bone fasteners 92 their full range of angular motion. Apertures 72, 74, 76, 78 can each include a beveled lower portion, such as beveled portions 72a, 76a of apertures 72, 76 shown in FIG. 6, to provide even greater clearance between upper surfaces 92c of heads 92b of fasteners 92. However, apertures 72, 74, 76, and 78 are smaller than the head of bone fasteners 92 so that, if the one of the bone fasteners 92 were to back out from its seat in plate 20, body 62 of retaining member 60 would contact the screw head to prevent further backing out and toggling. The tool engaging recess 92a in head 92b of each bone fastener 92 remains accessible through the corresponding aperture 72, 74, 76, 78 should it be desired to tighten a bone fastener 92 after installation of retaining member 60 without having to remove retaining member 60.

Referring now to FIGS. 8-13, another embodiment retaining member 100 will be discussed in further detail. Retaining member 100 has a general shape and size adapted to fit on plate 20, such as discussed above with respect to retaining member 60. Retaining member 100 includes a body 102 having first and second concave sides 104 and 106, and obliquely oriented first end 108 and second end 110. The size and shape of retaining member 100 thus corresponds in size and shape with plate 20. It is also contemplated that retaining member 100 can have a size and shape that is different than the size and shape of plate 20.

Body 102 of retaining member 100 includes an upper surface 102a and a lower surface 102b. Retaining member 100 also includes a pair of adjacent first and second engagement members 112 and 114 and a pair of adjacent third and fourth engagement members 116 and 118 extending from lower surface 102b of body 102. Engagement members 112, 114, 116, 118 are alignable with holes 32, 34, 36, 38, respectively, of plate 20 when retaining member 100 is secured thereto. Retaining member 100 further includes a first through-hole 120 adjacent first and second engagement members 112, 114, and a second through-hole 122 adjacent third and fourth engagement members 116, 118. Through-holes 120 and 122 can be provided with an enlarged upper portions 120a, 122b, respectively, to assist in providing locking fasteners 90 with a low profile along the upper surface 102a of retaining member 100. Through-holes 120, 122 can also have an intermediate thread pattern so that the locking fasteners are threadingly inserted therethrough.

Upper surface 102a of retaining member 100 has a slight convex curvature along longitudinal axis L2. Lower surface 102b is flat and is positionable against upper surface 22a of plate 20. Retaining member 100 has a thickness between upper surface 102a and lower surface 102b that adequately resists bending and other deformations that might be created by loads on retaining member 100 yet provide as low of a profile as possible above plate 20. Body 102 has a first groove 130 and a second groove 132 in lower surface 102b to impart some flexibility to body 102, allowing locking fasteners 90 to force engagement members 112, 114, 116 and 118 into engagement with the heads of bone fasteners 92 if necessary.

Retaining member 100 further includes a recessed surface 128 in upper surface 102a. Recessed surface 128 is flat and provides an attachment location for an insertion instrument. A central receptacle 124 and an adjacent alignment receptacle 126 extend between upper surface 102a and lower surface 102b. Receptacles 124, 126, like the receptacles of retaining member 60, provide locations for attachment and alignment of an insertion instrument with retaining member 100.

Figure 12:
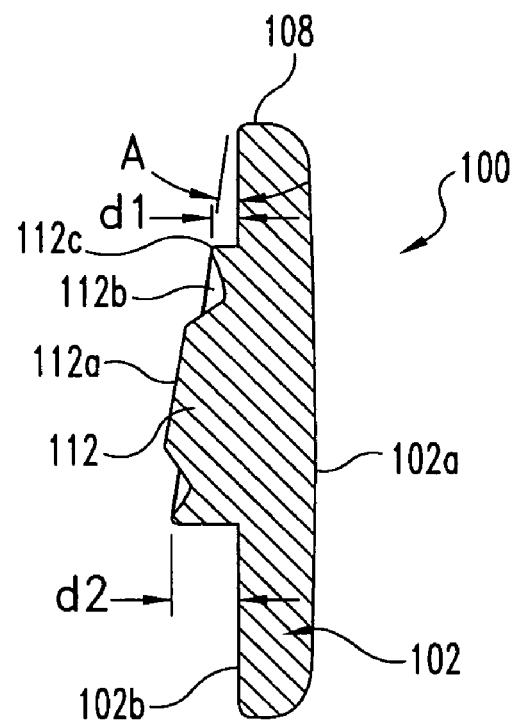
FIG. 12 is a sectional view of the retaining member of FIG. 8 through line 12-12 of FIG. 9.
Figure 13:
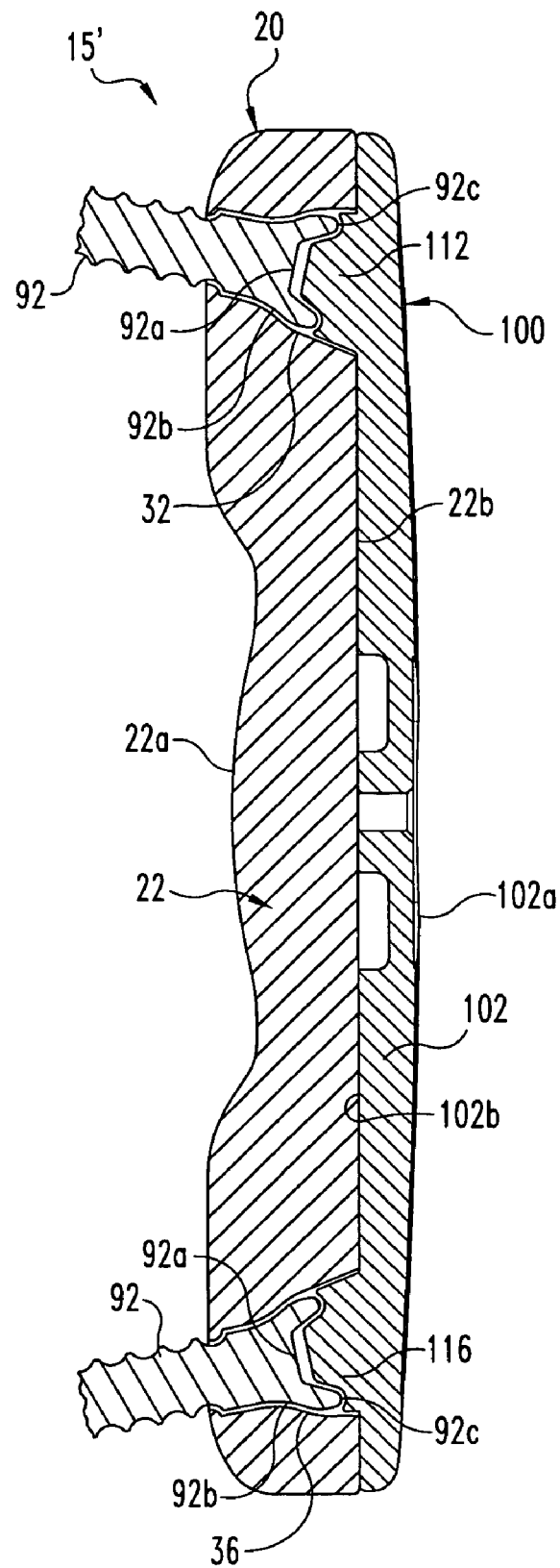
FIG. 13 is a sectional view of the plate of FIG. 1 with bone fasteners and a sectional view of the second embodiment retaining member along line 13-13 of FIG. 9 positioned adjacent to the upper surface of the plate and in engagement therewith.

Further details of engagement members 112, 114, 116, and 118 are provided in FIG. 12 with respect to engagement member 112. Engagement member 112 includes a central protrusion 112a positionable in the tool engaging recess 92a of bone fastener 92, as shown in FIG. 13. A recess 112b extends around central protrusion member 112a, and recess 112b is sized to receive upper surface 92c of head 92b of bone fastener 92. Central protrusion 112a is sized to engage bone fastener 92 in tool engaging recess 92a so that the sides of tool engaging recess 92a contact central protrusion 112a, fixing bone fastener 92 relative to plate 20.

The sidewall 112c of engagement member 112 is tapered at an angle such that the medial side of engagement member 112 extends a distance d2 from lower surface 102b, and the outer side of engagement member 112 extends a distance d1 from lower surface 102b. In this manner, the angle of engagement member 112 with the bottom surface 102b of body 102 corresponds to the angle of the head of bone fastener 92 through plate 20. This allows central protrusion 112a to be firmly seated in tool engaging recess 92a of bone fastener 92. Engagement members 114, 116 and 118 can similarly each include a central protrusion and recess therearound with tapered sidewalls for engaging the heads of bone fasteners 92.

A bone screw guide can be used to guide placement of the bone screws through the plate holes so that the heads of the bone screws are properly angled relative to plate 20 for engagement with engagement members 112, 114, 116 and 118. With the heads of the bone screws engaged by retaining element 100, the bone screws are fixed relative to plate 20. Engagement members 112, 114, 116 and 118 are received in the adjacent plate holes so that retaining member 100 can lie flush against the upper surface of plate 20, preventing tissue migration between retaining member 100 and the upper surface of plate 20 and minimizing the overall profile of the construct extending above the bony segment. As shown in FIG. 13, retaining member 100 extends above the upper surface of plate 20 and includes a thickness that provides sufficient stiffness to retaining member 100 to resisting bending forces and ensure positive fixation of the bone screws to prevent back out from the vertebra in which they are engaged.

Figure 14:
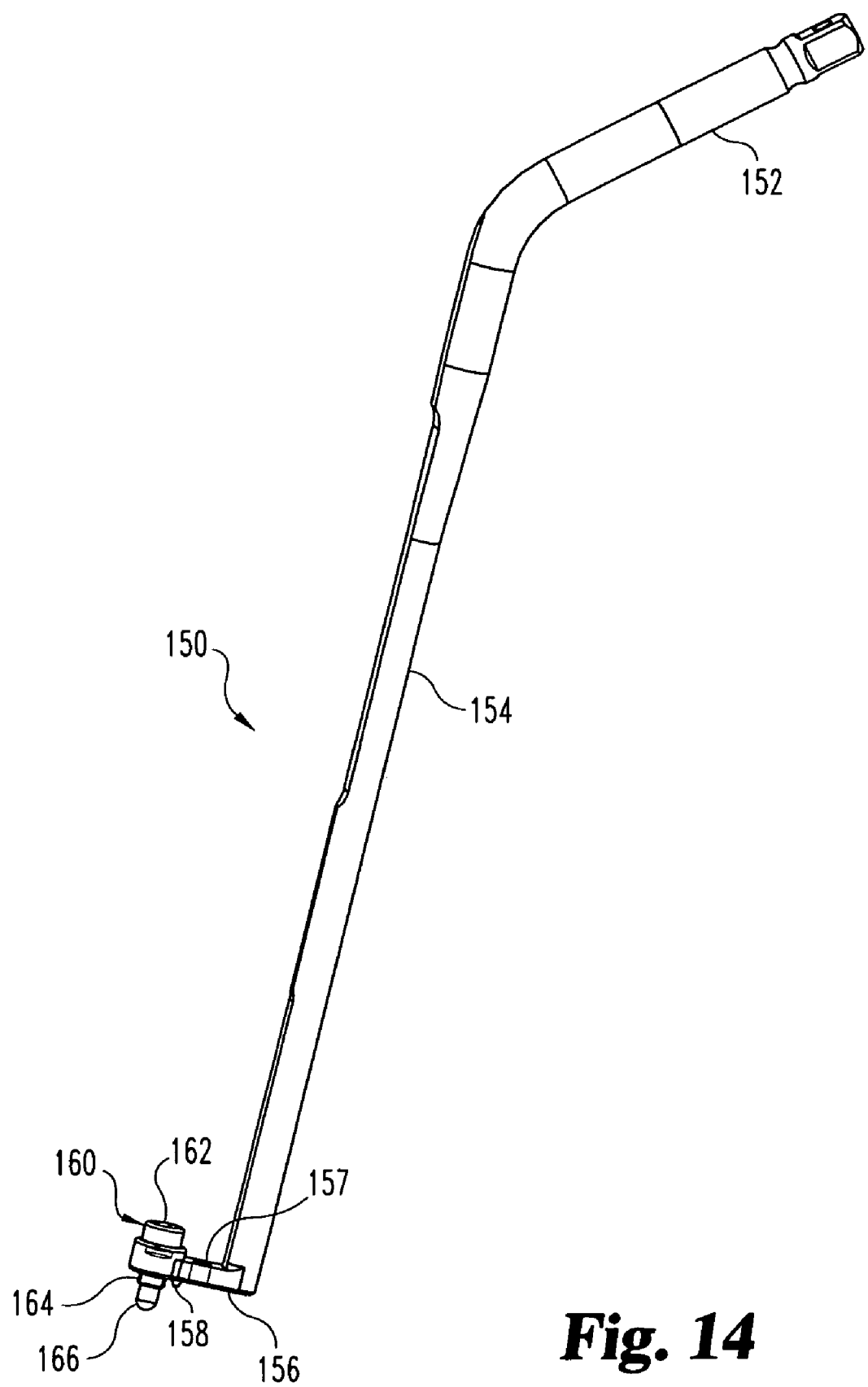
FIG. 14 is a perspective view of an instrument for inserting the plate and the retaining members to the surgical site.
Figure 15:
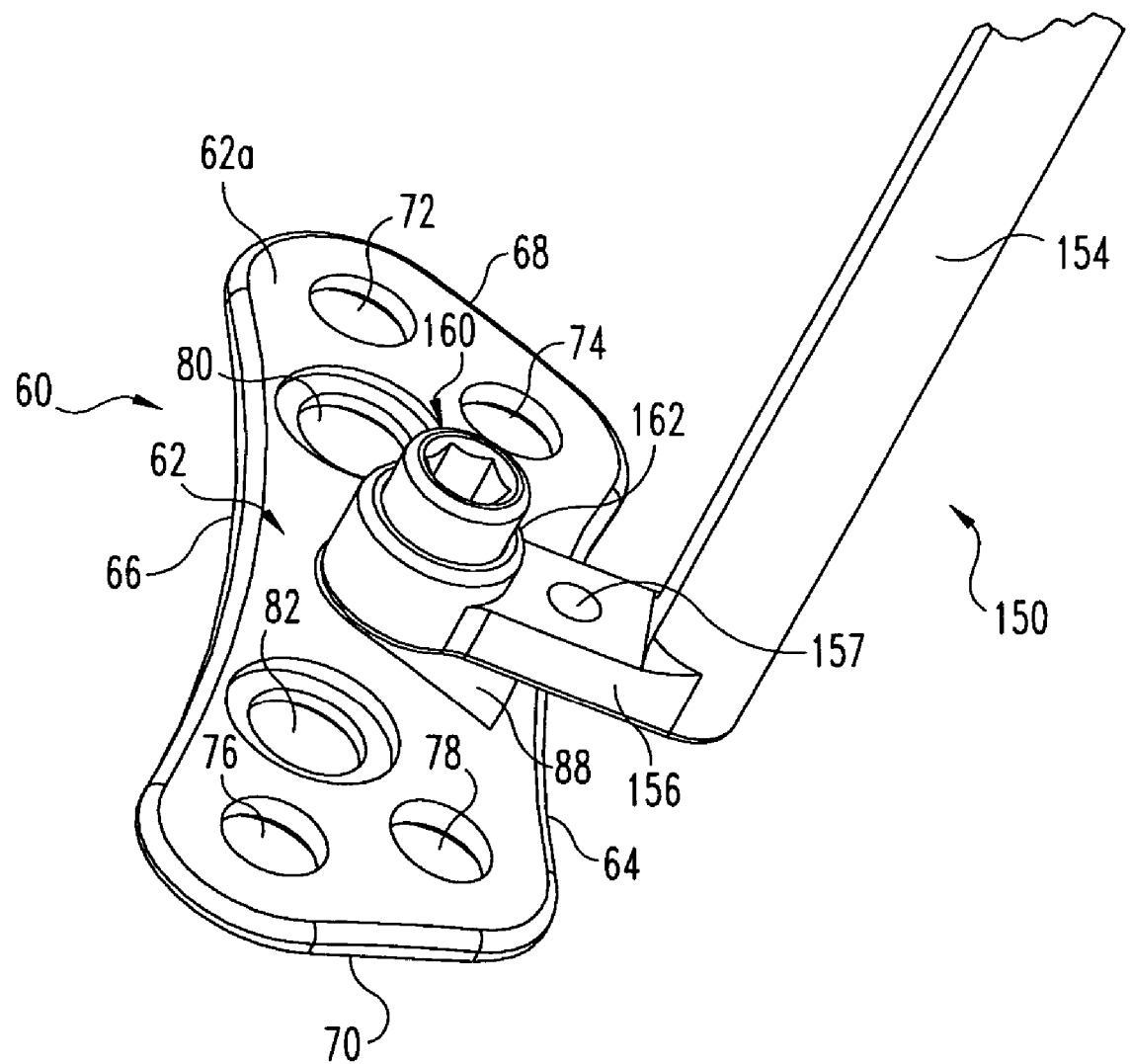
FIG. 15 is an enlarged perspective view of the distal end of the instrument of FIG. 14 attached to the retaining member of FIG. 4.

In FIG. 14, there is shown an insertion instrument 150 for inserting plate 20 to the surgical site and also for attaching retaining members 60, 100 to the inserted plate 20. In FIG. 15 there in shown retaining member 60 captured on the distal end of an insertion instrument 150, it being understood that retaining member 100 and plate 20 can also be attached to the distal end of instrument 150. Insertion instrument 150 aligns retaining member 60, 100 upon plate 20 and prevents rotation relative to plate 20 as the retaining member 60, 100 is attached thereto.

Insertion instrument 150 includes a proximal handle attachment end 152 and a shaft 154 extending distally from proximal end 152. Shaft 154 forms an angle with proximal end 152 so the handle attached at proximal end 152 is positioned away from the surgeon's approach to the surgical site. A distal foot 156 extends from the distal end of shaft 154 at a generally right angle thereto. Foot 156 includes an alignment member 158 extending distally therefrom and an adjacent attachment member 160. Attachment member 160 includes a head 162, an intermediate threaded portion 164 and a distal, non-threaded portion 166.

Insertion instrument 150 is removably attachable to plate 20 to position and hold plate 20 adjacent the bony segment before and during engagement therewith. Intermediate portion 164 threadingly engages central receptacle 44 and alignment member 158 is received in alignment receptacle 46 to ensure and maintain proper alignment of plate 20 on insertion instrument 150.

Insertion instrument 150 is also removably attachable to retaining members 60, 100 for positioning and engagement of the selected retaining member with plate 20. Intermediate portion 164 of attachment member 160 threadingly engages central receptacle 84 of retaining member 60 or central receptacle 124 of retaining member 100. Alignment member 158 is received in the corresponding alignment receptacle 86, 126 to ensure and maintain proper alignment of the selected retaining member 60, 100 on insertion instrument 150. Foot 156 is positioned along surface 88, 128 and is in bearing engagement therewith. As the selected retaining member 60, 100 is attached to plate 20, alignment member 158 is received in alignment receptacle 46 and distal end portion 166 is received in central receptacle 44. Intermediate portion 164 can be threadingly engaged with central receptacle 44 to provisionally capture the selected retaining member 60, 100 on plate 20. Alignment member 158 assists in preventing the selected retaining member 60, 100 from moving relative to plate 20 during attachment thereof with locking fasteners 90. Locking fasteners 90 are placed in respective ones of the through-holes 80, 82 of retaining member 60 or the through-holes 120, 122 of retaining member 100 to engage the retaining member to plate 20. Thereafter insertion instrument 150 is disengaged from plate 20 and also from the secured retaining member 60, 100.

It will be understood that variants in the design of instrument 150 described herein are contemplated. For example, the means for connecting and disconnecting plate 20 can be clippable/unclippable to cooperate with receptacle 44 of plate 20, or extend around or grasp one or more of the edges of plate 20 and/or the retaining members 60, 100.

Figure 16:
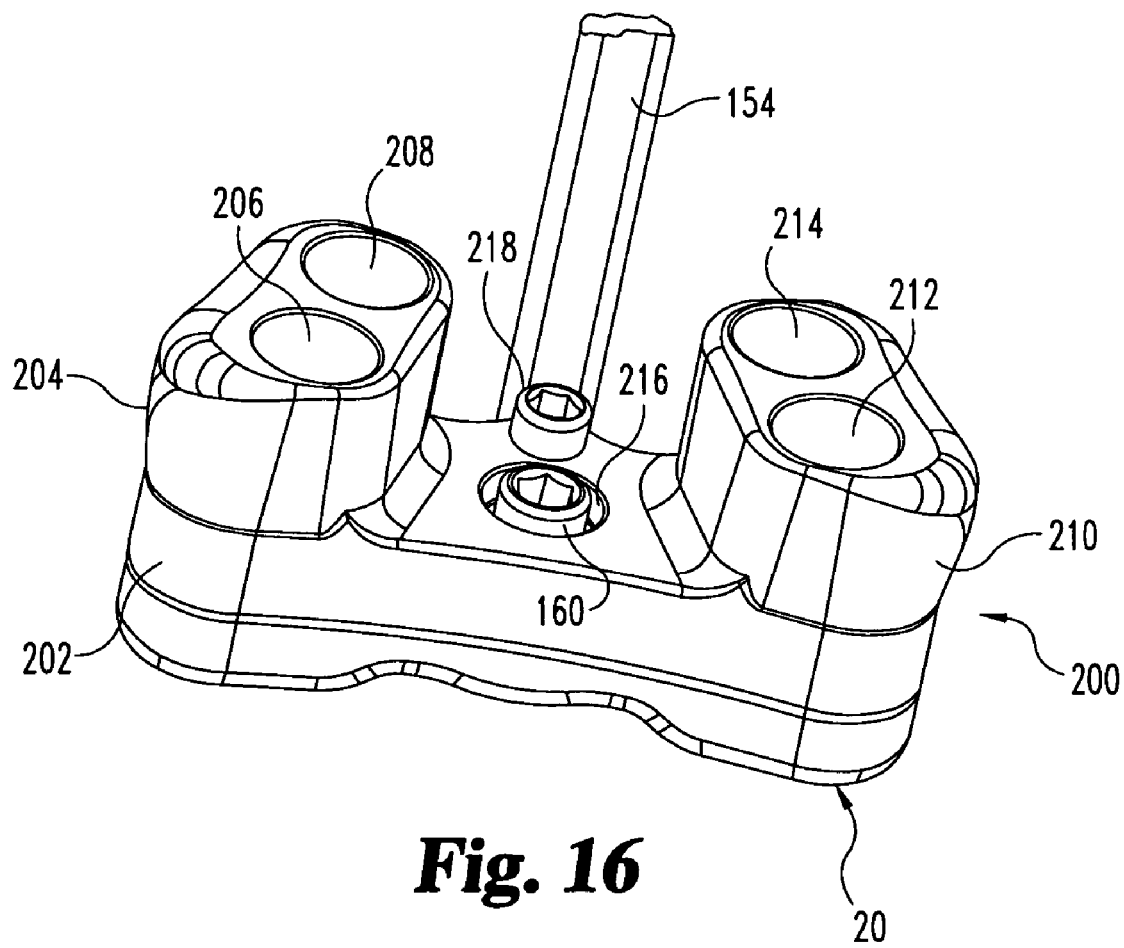
FIG. 16 is a perspective view of a guide mechanism positioned on the plate, the guide mechanism for guiding the drilling, tapping and/or insertion of fastener holes/fasteners to secure the plate to the bony segment.

Referring now to FIG. 16, there is shown an embodiment of a guide mechanism 200 for guiding a drill, tap and/or bone fastener through the holes of plate 20. In FIG. 16, plate 20 is attached to insertion instrument 150 with attachment member 160. Guide mechanism 200 includes a base 202 positionable against plate 20. Base 202 includes a receptacle 216 sized to receive attachment member 160, and the bottom surface of base 202 can include a recess to receive foot 156 so that base 202 can be position flush against upper surface 22a of plate 20. Base 202 further includes an opening for receiving fastener 218 therethrough. Fastener 218 engages hole 157 in foot 156 to secure guide mechanism 200 to insertion instrument 154.

Guide mechanism 200 includes a first guide member 204 at a first end thereof and a second guide member 210 at the opposite end thereof. First guide member 204 includes a first port 206 alignable with hole 32 of plate 20, and a second port 208 alignable with hole 34 of plate 20. Second guide member 210 includes a first port 212 alignable with hole 36 of plate 20, and a second port 214 alignable with hole 38 of plate 20. Ports 206, 208, 212, 214 provide elongated passages which receive and guide drilling, tapping and insertion instruments to provide the desired orientation for the bone engaging fasteners in their respective plate hole.

One example of a surgical method for attaching plate 20 to a bony segment includes attaching plate 20 to the distal end of an insertion instrument, such as instrument 150 discussed above. Plate 20 is positioned adjacent the bony segment in the desired orientation and position. With insertion instrument 150 positioning plate 20, the desired retaining element 60, 100 cannot be secured to plate 20 until insertion instrument 150 is removed. A drill guide such as drill guide 200 can be used to provide the desired orientation for the fastener holes drilled and/or tapped through plate 20 and/or for fastener insertion relative to plate 20. Bone fasteners 92 are then inserted through the plate and into any holes which have been drilled. Bone fasteners 92 are tightened by means of a screwdriver or the like to secure plate 20 to the bony segment. The optimum choice of the points of penetration and the values of the angles of penetration of bone fasteners 92 can be determined and adjusted by the surgeon before and during the procedure. With the plate secured to the bony segment, insertion instrument 150 is removed from plate 20, and then attached to the desired retaining member 60, 100 for engagement of the desired retaining member to plate 20.

It is contemplated that plates described herein can be provided in a kit with one or more retaining members, instruments for inserting the plate and retaining members, and guides for forming holes through the plate into the bony segment and for fastener insertion. For example, plate 20 can be provided with the requisite bone screws and insertion instrument, such as instrument 150, and drill guides, such as drill guide 200. Each of the retaining member embodiments 60, 100 can be provided to give the surgeon flexibility in selecting the desired means for securing plate 20 to the bony segment.

For example, retaining member 60 and bone fasteners 92, when secured to plate 20, allow the bone fasteners to pivot and compressive force to be maintained on the bony segment, or on one or more grafts, implants or other devices between adjacent portions of the bony segment. Retaining member 100 and bone fasteners 92, when secured to plate 20, fix the bone fasteners relative to plate 20 maintaining the spacing between the adjacent portions of the bony segment. Other embodiments contemplate a retaining member which combines elements of retaining member 60 and retaining member 100. For example, one end could be provided with apertures or other configuration to allow the fasteners to toggle in the plate, and the other end provided with engagement members the engage the fasteners to fix them relative to the plate. Other embodiments contemplate that the retaining members include two or more elements engageable to the plate. For example, a first retaining element of the retaining member could be engaged to the first portion of the plate, and a second retaining element of the retaining member could be engaged to the second portion of the plate.

Various fasteners are contemplated for securing the retaining members on the plate, such as clips, set screws, locking fasteners, and pins. It is also contemplated that the retaining members could be slidably or rotatably engaged to the plate and preloaded thereon. The present invention also contemplates retaining members secured by an interference fit with the plate or other attachment member attachable to the plate.

Examples of material which may be employed in fabrication of the plates and retaining members include any biocompatible non-resorbable material, such as titanium, stainless steel, shape memory alloys, and combinations thereof. Resorbable materials are also contemplated. The retaining members, plate and fasteners can be made from the same material or different material. The plate assembly may also be used in combination with various types of implants. For example, in spinal surgery such implants include interbody spacers, fusion device, and bone graft materials that are placed in disc space D. Further examples of such devices include bone dowels, push-in cages, screw-in cages, tapered cages, cages filled with bone graft and/or graft substitute material or other types of devices suitable for such fusion applications, external or internal stabilization of a segment of the spinal column or other bony segment.

While the invention has been illustrated and described in detail in the drawings and foregoing description, the same is to be considered as illustrative and not restrictive in character, it being understood that only preferred embodiments have been shown and described and that all changes and modifications that come within the spirit of the invention are desired to be protected.

What is claimed is:

1. A plating system for stabilization of a bony segment, comprising:
   a plate including:
     a first portion with a first hole and a second hole therethrough between an upper surface of said plate and a lower surface of said plate;
     a second portion with a third hole and a fourth hole therethrough between an upper surface of said plate and a lower surface of said plate;
   bone fasteners positionable in each of said first, second, third and fourth holes to secure said plate to the bony segment, each of said bone fasteners including a head with a tool engaging recess, each of said heads when positioned in respective ones of said first, second, third and fourth holes being located entirely below said upper surface of said plate adjacent said holes; and a retaining member engageable to said plate and extending at least partially over each of said bone fasteners, said retaining member having at least first, second, third and fourth engagement members extending therefrom and into a corresponding one of said first, second, third and fourth holes and engaging said tool engaging recess of said bone fastener in said hole to fix said bone fasteners relative to said plate, wherein each of said engagement members includes a sidewall extending from a lower surface of said retaining member, a central protrusion positionable in said tool engaging recess of said bone fastener, and a recess between said sidewall and said central protrusion that extends around said central protrusion and is sized to receive said head of said bone fastener therein, wherein said sidewall of each of said engagement members is tapered so that a first side of said sidewall extends from said lower surface of said retaining member a greater distance than an opposite side of said sidewall to angle said engagement member relative to said lower surface of said retaining member, wherein said engagement members are situated on said retaining member so that said that said first and second engagement members taper away from said second portion of said plate toward a first end of said retaining member and said third and fourth engagement members taper away from said first portion of said plate toward a second end of said retaining member opposite said first end.

2. The system of claim 1, wherein said plate is positionable with respect to a spinal column segment so that said first and second holes are located over an upper vertebra and said third and fourth holes are located over a lower vertebra.

3. The system of claim 1, wherein said retaining member includes a pair of grooves in a lower surface thereof, said grooves extending transversely to a longitudinal axis of said retaining member.

4. The system of claim 1, wherein said retaining member substantially covers said upper surface of said plate.

5. The system of claim 1, wherein said plate includes a first bore adjacent said first and second holes and a second bore adjacent said third and fourth holes, said retaining member includes a first through-hole positionable over said first bore and a second through-hole positionable over said second bore, and further comprising first and second fasteners positionable through respective ones of said first and second through-holes and engageable in respective ones of said first and second bores of said plate to engage said retaining member to said plate.

6. The system of claim 5, wherein:
said plate includes an insertion tool engagement receptacle and an alignment receptacle adjacent to said insertion tool engagement receptacle, each of which opens at said upper surface of said plate; and
said retaining member includes an insertion tool engagement receptacle and an alignment receptacle adjacent to said insertion tool engagement receptacle, each of which is in communication with a respective one of said insertion tool engagement receptacle and said alignment receptacle of said plate.

7. The system of claim 1, wherein said retaining member is positioned against said upper surface of said plate.

8. The system of claim 1, wherein said retaining member extends above said upper surface of said plate.

9. The system of claim 1, wherein each of said first, second, third and fourth holes includes a spherically shaped seat and said head of each of said bone fasteners includes a spherical lower surface positionable in said seat.

10. A plating system for stabilization of a bony segment, comprising:
a plate including:
a first portion with at least a first hole and a second hole therethrough between an upper surface of said plate and a lower surface of said plate;
a second portion with at least a third hole and a fourth hole therethrough between an upper surface of said plate and a lower surface of said plate;
bone fasteners in each of said first, second, third and fourth holes to secure said plate to the bony segment, each of said bone fasteners including a head with a recess, each of said heads being located entirely below said upper surface of said plate adjacent said holes; and
a retaining member engaged to said plate and extending at least partially over each of said bone fasteners, said retaining member having at least first, second, third and fourth engagement members extending therefrom and into a corresponding one of said recesses of said bone fasteners in said holes to fix said bone fasteners relative to said plate, wherein each of said engagement members includes a sidewall extending from a lower surface of said retaining member and said sidewall is tapered so that a first side of said sidewall extends from said lower surface of said retaining member a greater distance than an opposite side of said sidewall to angle said engagement member relative to said lower surface of said retaining member, wherein said first side of said sidewall is oriented toward a middle of said retaining member and said opposite side of said sidewall is oriented toward an adjacent end of said retaining member so that each of said sidewalls tapers from said middle of said retaining member toward and adjacent end of said retaining member.

11. The system of claim 10, wherein said plate is positionable with respect to a spinal column segment so that said first and second holes are located over an upper vertebra and said third and fourth holes are located over a lower vertebra.

12. The system of claim 10, wherein said retaining member includes a pair of grooves in a lower surface thereof, said grooves extending transversely to a longitudinal axis of said retaining member.

13. The system of claim 10, wherein said retaining member substantially covers said upper surface of said plate.

14. The system of claim 10, wherein said plate includes a first bore adjacent said first and second holes and a second bore adjacent said third and fourth holes, said retaining member includes a first through-hole positionable over said first bore and a second through-hole positionable over said second bore, and further comprising first and second fasteners positionable through respective ones of said first and second through-holes and engageable in respective ones of said first and second bores of said plate to engage said retaining member to said plate.

15. The system of claim 10, wherein each of said engagement members includes a central protrusion positionable in said recess of said corresponding bone fastener and a recess between said sidewall and said central protrusion, said recess extending around said central protrusion receiving said head of said bone fastener therein.

16. The system of claim 14, wherein:
said plate includes an insertion tool engagement receptacle and an alignment receptacle adjacent to said insertion tool engagement receptacle, each of which opens at said upper surface of said plate; and
said retaining member includes an insertion tool engagement receptacle and an alignment receptacle adjacent to said insertion tool engagement receptacle, each of which is in communication with a respective one of said insertion tool engagement receptacle and said alignment receptacle of said plate.

17. The system of claim 10, wherein said retaining member is positioned against said upper surface of said plate.

18. The system of claim 10, wherein said retaining member extends above said upper surface of said plate.

19. The system of claim 10, wherein each of said first, second, third and fourth holes includes a spherically shaped seat and said head of each of said bone fasteners includes a spherical lower surface positionable in said seat.

20. A plating system for stabilization of a bony segment, comprising:
a plate including a first portion alignable with a first vertebra and said first portion having a first hole therethrough between an upper surface of said plate and a lower surface of said plate and said plate extending to a second portion alignable with a second vertebra and said second portion having a second hole therethrough between an upper surface of said plate and a lower surface of said plate;
bone fasteners positionable in each of said first and second holes to secure said plate to respective ones of the first and second vertebrae, each of said bone fasteners including a head with a tool engaging recess, each of said heads when positioned in respective ones of said first and second holes being located with said tool engaging recess below said upper surface of said plate adjacent said holes; and
a retaining member engageable to said plate and extending at least partially over each of said bone fasteners, said retaining member having at least first and second engagement members extending therefrom adjacent opposite ends of said retaining member and into a corresponding one of said first and second holes and engaging said tool engaging recess of said bone fastener in said hole to fix said bone fasteners relative to said plate, wherein said retaining member includes a pair of grooves in a lower surface thereof between said first and second engagement members, said grooves extending transversely to a longitudinal axis that extends from one of said opposite ends to the other of said opposite ends of said retaining member, said grooves imparting flexibility to said retaining member to force said engagement members into said recesses of said bone engaging fasteners when said retaining member is engaged to said plate.

* * * * *